United States Patent [19]

O'Connor

[11] 4,328,424
[45] May 4, 1982

[54] IONIZATION DETECTOR CHAMBER

[75] Inventor: Dennis R. O'Connor, Rochdale, England

[73] Assignee: Chloride, Incorporated, Tampa, Fla.

[21] Appl. No.: 58,613

[22] Filed: Jul. 18, 1979

Related U.S. Application Data

[63] Continuation of Ser. No. 810,889, Nov. 14, 1978.

[30] Foreign Application Priority Data

Jul. 2, 1976 [GB] United Kingdom ............... 27668/76
Sep. 20, 1976 [GB] United Kingdom ............... 38825/76

[51] Int. Cl.³ ............................................. G01T 1/18
[52] U.S. Cl. ..................................... 250/384; 250/385
[58] Field of Search ............... 250/381, 382, 384, 385, 250/389

[56] References Cited

U.S. PATENT DOCUMENTS 4,044,263 8/1977 Ried, Jr. et al. ................... 250/381

Primary Examiner—Alfred E. Smith
Assistant Examiner—Janice A. Howell
Attorney, Agent, or Firm—Robert E. Ross

[57] ABSTRACT

This invention is a smoke detector for giving a warning that a fire is imminent. The detector has an ionization chamber with a central electrode which is covered by insulation except at a restricted area closely spaced from a measuring electrode, a second electrode being constituted by a perforated wall of the ionization chamber. The detector is very sensitive to the presence of smoke, because of the concentration of the electric field in the area between the measuring electrode and the exposed part of the first electrode.

9 Claims, 3 Drawing Figures

IONIZATION DETECTOR CHAMBER

This is a continuation of application Ser. No. 810,889, filed Nov. 14, 1978.

This invention relates to a detector including an ionisation chamber for example for detecting the presence of smoke so as to be capable of giving a signal for giving an alarm that a fire is imminent in a building.

An object of the invention is to provide a simply constructed small detector which is nevertheless very sensitive to the presence of smoke.

According to the present invention a detector including an ionisation chamber has first and second electrodes, the exposed conducting area of the first of which is restricted, and a measuring electrode disposed adjacent the said exposed area, together with means for ionising gas in the chamber including the space between the three electrodes.

The dispostion of the measuring electrode in relation to the first electrode concentrates the electric field within the part of the chamber adjacent to one electrode, and ensures that the presence of smoke has a much greater effect on the ionisation current flowing between the measuring electrode and the other electrode than on the ionisation current flowing between the first electrode and the measuring electrode.

The first electrode preferably comprises a rod extending into the chamber, and surrounded by an insulating sleeve except for the exposed area which is at its inner end. The insulating sleeve is preferably around the sides of the first electrode, except for a short length of the sides of the inner end.

The first electrode can be positioned concentrically within the other electrode constituting the ionisation chamber wall, and that effectively divides the space within the chamber into two areas, a central area between the measuring electrode and the exposed area of the first electrode, and a larger surrounding area between the measuring electrode and the wall of the ionisation chamber.

The ionisation means is conveniently a piece of radioactive material for example a foil of radium or americium and that can be positioned anywhere in the ionisation chamber although a convenient position is on the measuring electrode centrally opposite the exposed part of the first electrode.

In one preferred construction the chamber has an insulating base carrying the measuring electrode which in turn carries a foil of americium; the ionisation chamber consists of an upstanding wall around the base and an end wall closing the chamber, all those walls being perforated while the first electrode extends through the end wall of the ionisation chamber in the form of a cylindrical conducting rod which is a tight fit within an insulating sleeve.

The sensitivity of the detector may not be accurately reproducable from sample to sample if the dielectric constant of the insulation material varies from sample to sample. The critical region of the detector is the region of high electric field between the first electrode and the measuring electrode and by terminating the insulation short of the end of the elongate first electrode so that the last part of the length of its sides is not covered by insulation the insulation is removed from this region of high electric field and in consequence variations in the dielectric constant are not reflected in substantial variations in the sensitivity of the detector. The detector is also made more sensitive as the surface area of the exposed end of the elongat first electrode is larger. This modifies the electric field pattern in the region between the first electrode and the measuring electrode, so giving increased sensitivity.

The insulation must extend reasonably near to the end of the elongate electrode to prevent the lines of the electric field going directly from the positive electrode to a surrounding negative electrode rather than by way of the measuring electrode.

The invention may be carried into practice in various ways, and one embodiment will now be described by way of example with reference to the accompanying drawings of which;

Figure 1:
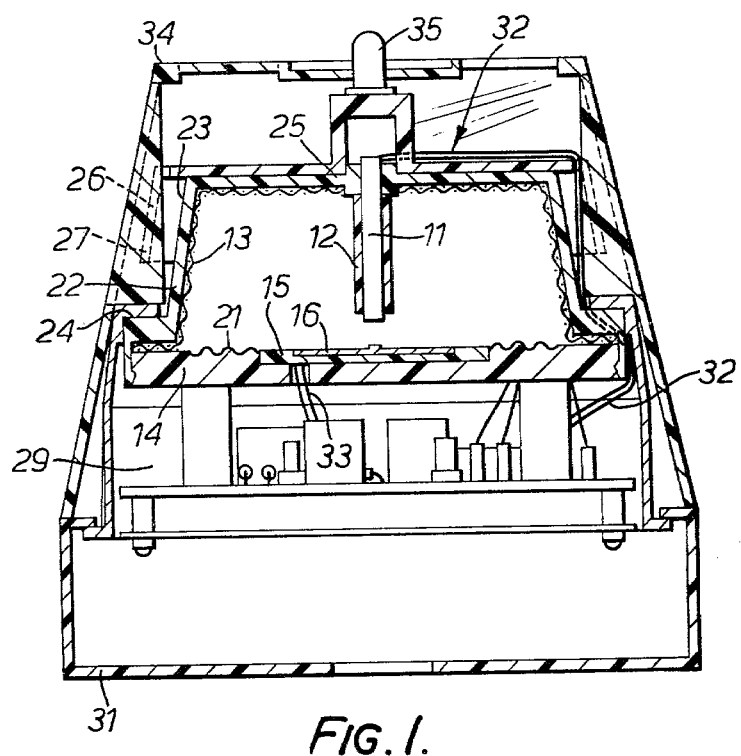
FIG. 1 is a sectional elevation of an ionisation type smoke detector.
Figure 2:
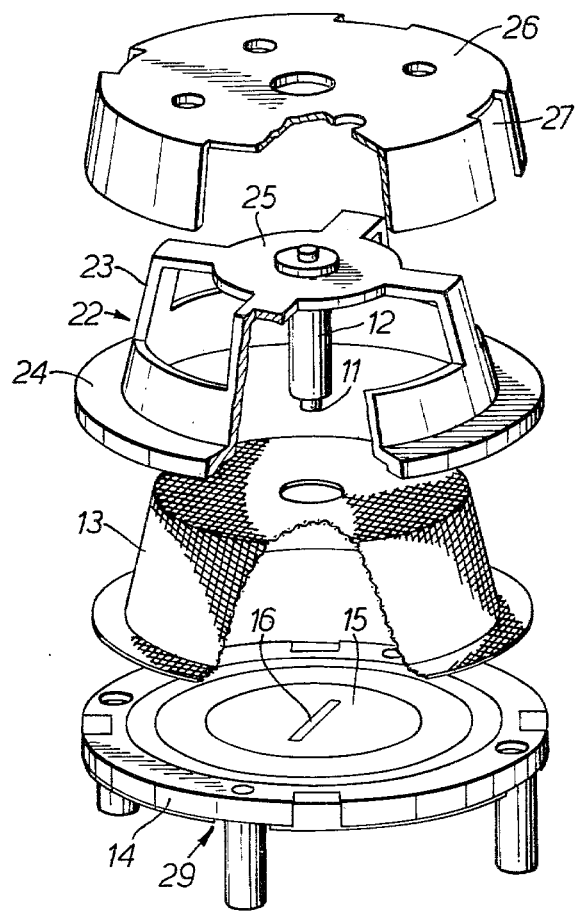
FIG. 2 is an exploded view of components of the detector.

The detector includes an ionisation chamber consisting of the space between an insulating base 14 and a perforated wall 13 upstanding from the sides of the base 14 with an enclosed top. A measuring electrode 15 is mounted in a central recess in the base 14 and centrally mounted on the exposed face of the measuring electrode 15 is an elongate foil 16 of americium.

Closely spaced centrally from the foil 16 is the exposed end of a cylindrical electrode 11 which is a close fit within an insulating sleeve 12 which serves to mount the electrode 11 in, and insulate it from, the top wall of the chamber 13.

The insulation 12 extends down the larger part of the length of the sides of the elongate cylindrical rod electrode 11 but terminates a little short of the exposed end of that electrode. This means that the insulation is removed from the region of high intensity field between the electrodes 11 and 15 so that the sensitivity of the detector does not depend to any substantial degree on the dielectric constant of the material of the insulating sleeve 12. The sleeve terminates sufficiently near the end of the electrode 1 to prevent the lines of electric field passing directly from the first electrode to the second electrode rather than by way of the measuring electrode 15.

In order to prevent excessive leakage currents from measuring electrode 15 to the second electrode 13 over the surface of the insulating base 14, a conducting guard ring could be fitted in an annular groove in the upper surface of the base surrounding the disc 15 and within the perforated wall 13.

The surface of the base 14 between the measuring electrode 15 and the perforated wall 13 constituting the negative electrode is corrugated at 21 to increase the length of the creep path over insulation between those electrodes.

The perforated wall 13 is part of a sub-assembly constituting the outer wall of the ionisation chamber, and comprising three components. The perforated wall 13 is a simple mesh cup with a top having a central aperture for the insulator 12, and a frusto-conical side wall, and that fits within an inner moulding 22 having four radially directed retaining ribs 23, extending from a rim 24 to a central disc 25, and then there is an outer moulding 26 fitting around the apertured part of the inner moulding 23 and having four equally circumferentially spaced slots in its frusto-conical side wall, as indicated at 27, which are opposite the ribs 23. The arrangement allows ambient air free access to the ionisation chamber within the wall 13, while yet there is no direct passage for air to enter without having to deviate around the ribs.

Electrical circuit components are contained in a chamber 29 below the base 14, and within a lower wall 31, and electrical connections 32 respectively from the electrodes 11 and 13 are led down around the sub-assembly 24, 26, into the chamber 29. A connection from the measuring electrode 15 extends directly into the chamber 29, as indicated at 33, and if there is a guard ring, as described above, the connection from that also would extend through the base 14.

There is a surrounding casing 34 having slots for entry of the air, and a lamp 35 can be seen from a central hole in the top of the cover 34 for giving a visual indication of an alarm. That lamp is connected to the circuit components in the chamber 29.

Figure 3:
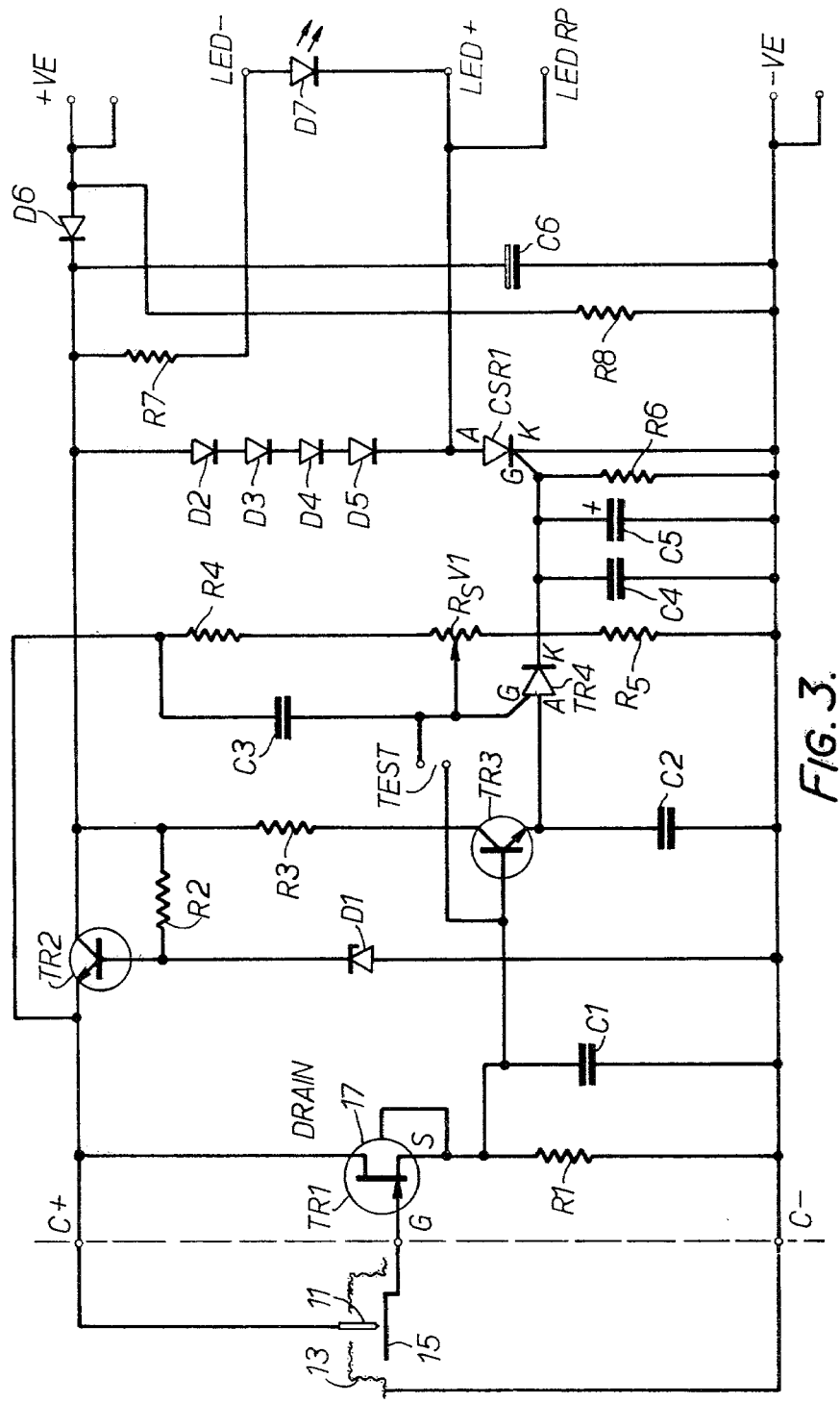
FIG. 3 is a circuit diagram of the detector.

The circuit diagram is shown in FIG. 3, and it can be seen the electrodes 11 and 13 are connected respectively to the drain and source electrode of a field effect transistor 17, while the gate electrode of the F.E.T is connected to the measuring electrode 15. The circuit is conventional, and operates so that as the voltage on the measuring electrode 15 arise, the drain to source current in the field effect transistor 17 increases, so that the voltage across a resistor R1 also increases and this voltage also appears on the base of transistor TR3 which converts the voltage to a low impedance signal capable of triggering a transistor TR4 which is a programmable unijunction transistor (PUT). TR4 will only trigger, firing the output thyristor CSR1, if the input at A on TR4 exceeds the threshold voltage determined by the setting of a potentiometer RV1. When CSR1 is fired, the current through the detector increases and is usually limited by the circuit in the fire alarm control panel. This constitutes the alarm signal and a local indication is given of the switching of the detector to the alarm condition by the illumination of the lamp 35 which is a light emitting diode D7.

Thus an alarm is given in dependence on the voltage of the measuring electrode 15, and the operation of the detector is such that ionisation current flows between the electrodes under the influence of the electric field in the ionisation chamber, and the voltage of the measuring electrode 15 is an intermediate voltage determined by the relationship of the impedance between the electrodes 11 and 15, to that between the electrodes 15 and 13.

Under normal conditions, that is with no smoke present in the chamber, the ratio of the impedance between the electrodes 11 and 15 to the impedance between the electrodes 15 and 13 will be set by the electric field concentrations in the two parts of the chamber. These concentrations are in turn determined by the sizes, shapes and spacing of the electrodes. Thus the chamber can be considered to constitute an inner part between the positive electrode 11 and the measuring electrode 15 and a surrounding outer part between the measuring electrode 15 and the negative electrode 13.

The relationship of the measuring electrode 15 to the positive electrode 11 serves to concentrate the electric field at that region because substantially all the lines of electric field flow to the restricted exposed end of the electrode 11 rather than through the insulation to the sides of that electrode Thus when smoke appears within the ionisation chamber, ions attach themselves to smoke particles and lose their mobility. The effect is much more pronounced in the larger region between the measuring electrode 15 and the negative electrode 13, than between the positive electrode 11 and the measuring electrode 15, and the effect is for the impedance of the outer part of the chamber to increase so that the voltage on the measuring electrode 15 increases to the threshold value if the smoke concentration is sufficiently great.

This gives good sensitivity for getting a response from the field effect transistor from quite a small ionisation chamber and the construction is imple because a single piece of radioactive material suffices for both parts of the chamber.

In addition there is only one high impedance leakage path that could affect the detector's sensitivity, i.e. over the insulator 14 between electrodes 15 and 13. If this is corrugated as at 21 or protected with a guard ring as described above, or both, the detector will be more immune to contamination by duct and dirt than are more conventional detectors employing two or more high impedance paths.

I claim:

1. A detector including an ionization chamber having a first electrode comprising a rod extending into the chamber and terminating at a free end, a shielding sleeve disposed about the entire length of the rod except for the extreme portion of the free end, a measuring electrode disposed closely adjacent the free end of the rod and a second electrode disposed further away from the first electrode and the measuring electrode that the measuring electrode is spaced from the first electrode, and an ionization source in said chamber.

2. A detector as set out in claim 1 in which the ionization source is disposed centrally of the measuring electrode adjacent the free end of the rod.

3. A detector as set out in claim 1 in which said shielding means comprises an insulating sleeve.

4. A detector as set out in claim 1 in which said second electrode conforms generally to the wall of the chamber.

5. A detector including an ionization chamber having two current electrodes, a measuring electrode, and an ionization source, a first current electrode comprising a rod extending into the chamber and terminating at a free end in the chamber, the measuring electrode being disposed in the chamber closely adjacent the free end of the rod, said measuring electrode lying generally in a plane perpendicular to the axis of the rod and having an area substantially greater than the cross-sectional area of the rod, the ionization source being disposed centrally of the measuring electrode and substantially in alignment with the rod, whereby a high intensity electric field is formed between the end of the rod and the measuring electrode, and a second current electrode has a portion disposed in lateral spaced relation to said rod at a distance such that a low intensity electric field is produced between the measuring electrode and said portion of the first electrode, and means is disposed around all of said rod in the chamber except the extreme free end portion to prevent appreciable current flow directly between the rod and the second electrode.

6. A detector as set out in claim 5 in which the means disposed around the rod is an insulating sleeve.

7. A detector as set out in claim 5 in which said second electrode conforms generally to the peripheral wall of the chamber.

8. A detector including a peripheral wall forming a first current electrode, a base closing one end of the wall, an ionization source centrally located on the base, a measuring electrode on the base surrounding the ionization source and a rod forming a second current electrode extending into the chamber from the end of the wall opposite the base, the distal end of the rod being disposed closely adjacent the ionization source and centrally of the measuring electrode, and an insulating sleeve covering all of said rod except the distal end portion, whereby in operation a high intensity field exists between the distal end of the rod and the measuring electrode, a low intensity field exists between the measuring electrode and the wall comprising the first electrode, and substantially no current flows directly between the first and second electrode.

9. An ionization detector enclosure, including a peripheral wall having means permitting the entry of ambient air, a support within the enclosure, an ionization source disposed on said support centrally of said chamber, a measuring electrode surrounding said ionization source in radial spaced relation thereto, a first current electrode having its only exposed surface disposed closely adjacent the ionization source and centrally of the measuring electrode, and a second current electrode surrounding the measuring electrode, the components being so positioned and dimensioned that in operation, a first region of high intensity field is formed between the first current electrode and the measuring electrode, and a second region of low intensity field is formed between the measuring electrode and the second current electrode, the volume of the second region surrounding the first region and being substantially greater than the volume of the first region whereby smoke entering through the wall encounters the second region before the first region.

* * * * *